United States Patent
Boice et al.

(10) Patent No.: US 6,998,488 B2
(45) Date of Patent: Feb. 14, 2006

(54) PROCESS AND INTERMEDIATES FOR THE PREPARATION OF 4-ARYL PIPERIDINES

(75) Inventors: Genevieve N. Boice, Astoria, NY (US); Karen M. Conrad, Garwood, NJ (US); Edward G. Corley, Old Bridge, NJ (US); Louis Matty, Jr., Basking Ridge, NJ (US); Jerry A. Murry, New York, NY (US); Cecile G. Savarin, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 143 days.

(21) Appl. No.: 10/795,840

(22) Filed: Mar. 8, 2004

(65) Prior Publication Data

US 2004/0181070 A1    Sep. 16, 2004

Related U.S. Application Data

(60) Provisional application No. 60/453,454, filed on Mar. 10, 2003.

(51) Int. Cl.
*C07D 211/14* (2006.01)
*C07D 211/82* (2006.01)

(52) U.S. Cl. ............... 546/228; 546/326; 546/233; 546/230; 546/226

(58) Field of Classification Search ............ 546/226, 546/230, 233, 228, 326
See application file for complete search history.

(56) References Cited

FOREIGN PATENT DOCUMENTS

| EP | 0 831 087 | 9/1997 |
|---|---|---|
| WO | WO 02/068387 | 9/2002 |
| WO | WO 02/068388 | 9/2002 |

OTHER PUBLICATIONS

Ca 83:206332, "Benzoguanamine derivatives", Murai et al.*
Ca 133:350205, "Contraceptive compositions containing antiprogestinic and progestinic dihydro-2H-3,1-benzoxazin-2-ones", Gary et al.*
Ca 2002:224612, "Combination regimens using progesterone receptor modulators", Grubb et al.*
Billotte, Synlett (1998), pp. 379-380, "Synthesis of C-Substituted cyclic amines using azacycloalkyl organozinc reagents".
Comins et al., J. Org. Chem. (1982), vol. 47, pp. 4315-4319, "Regioselective addition of Grignard reagents to 1-acylpyridinium salts".

* cited by examiner

*Primary Examiner*—Charanjit S. Aulakh
(74) *Attorney, Agent, or Firm*—Baerbel R. Brown; Melvin Winokur

(57) ABSTRACT

A novel process is provided for the preparation of 4-aryl piperidines, and the useful intermediates obtained therein. These compounds are intermediates for the synthesis of melanocortin-4 receptor (MC-4R), which are useful for the treatment of disorders such as obesity, diabetes, male sexual dysfunction, and female sexual dysfunction.

35 Claims, No Drawings

PROCESS AND INTERMEDIATES FOR THE PREPARATION OF 4-ARYL PIPERIDINES

This application claims benefit of provisional application 60/453,454 filed Mar. 10, 2003.

BACKGROUND OF THE INVENTION

The present invention provides a process for the preparation of 4-aryl piperidines of general formula (I).

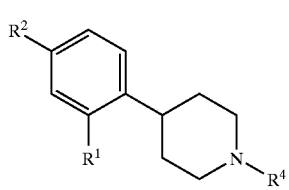

(I)

The present invention also provides intermediates useful in the disclosed process.

The compounds of formula I are intermediates useful for the preparation of the 4-aryl piperidine compounds of the general formula II, wherein X is aryl and Y is hydrogen or fluoride.

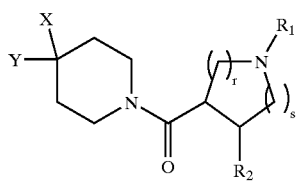

(II)

The compounds of formula II, along with their use as melanocortin receptor agonists, were disclosed in WO 02/068388, (published on Sep. 6, 2002). The compounds of formula II are also useful as agents for the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity, diabetes mellitus, hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction, fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor (MC-4R) relative to MC-1R, MC-2R, MC-3R, and MC-5R, which makes them especially useful in the prevention and treatment of obesity, as well as male and/or female sexual dysfunction, including erectile dysfunction.

WO 02/068388, (published on Sep. 6, 2002) describes processes for preparing the compounds of formula II. However, a large number of synthetic transformations are required (the longest linear sequence being about 13 steps) with an overall yield of less than 10%. Additionally, explosive reagents, such as zinc azide were required.

With the present invention, there is produced more efficiently the compound of structural formula I in considerably fewer chemical steps utilizing fewer and less expensive chemical reagents. The longest linear synthetic sequence comprises 4 steps with a higher overall yield.

The preparation and coupling of acyl pyridinium ions is described in Comins, D. L., *J. Org. Chem.*, vol. 47, pp. 4315–4319 (1982). The preparation and reduction of dihydropyridine rings is described in European Patent Application No. 831087 (1998).

SUMMARY OF THE INVENTION

This invention is concerned with a process for preparing compounds of structural formula (I) and certain useful intermediates obtained during that process.

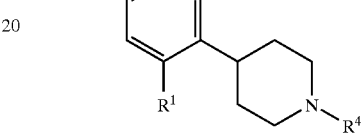

(I)

The novel process and novel intermediates can be exemplified in Scheme A, which shows the preparation of 4-aryl piperidine (I). The process involves the halogenation of the substituted aryl (III) to form (IV). The piperidine ring equivalent is introduced via a Grignard reaction. The aryl halogen (IV) is treated with a magnesium reagent to form the aryl magnesium halide (V). The resulting aryl magnesium halide (V) is added to a preformed acyl pyridinium ion to afford dihydropyridine (VI). The dihydropyridine ring of compound (VI) is reduced to the corresponding $R^3$ protected piperidine (VII). The $R^3$ protecting group of (VII) may be cleaved to give the free amine (VIII), which may subsequently be re-protected with another protecting group, $R^4$, to give the compound of structural formula (I).

Scheme A

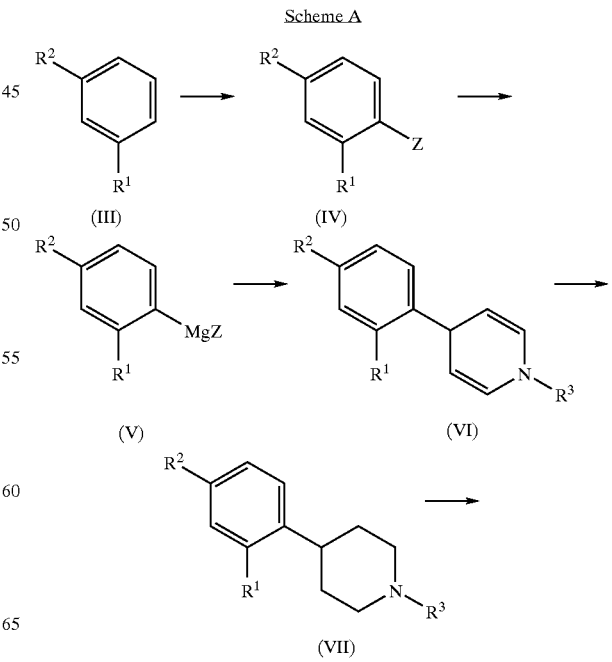

-continued

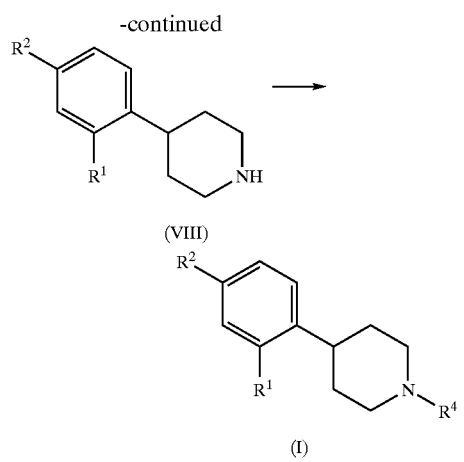

$R^1$, $R^2$, $R^3$, $R^4$, and Z are as defined below.

Alternatively, as shown in Scheme B, the $R^3$ protected dihydropyridine (VI) may be converted directly to the $R^4$ protected piperidine (I) by reducing the dihydropyridine ring in the presence of Boc anhydride.

Scheme B

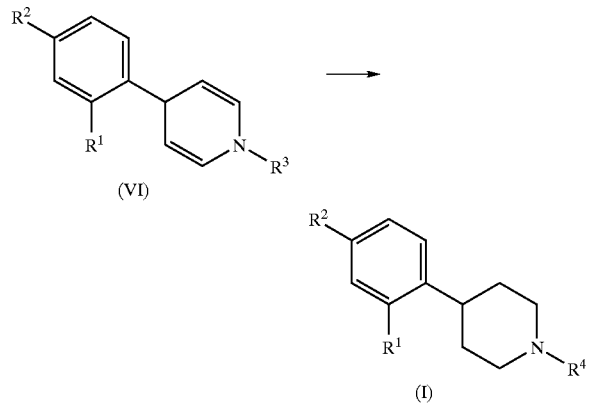

$R^1$, $R^2$, $R^3$, $R^4$, and Z are as defined below.

Also provided are intermediate compounds which are useful for the preparation of compounds of structural formula (I).

DETAILED DESCRIPTION OF THE INVENTION

The present invention provides a process for the preparation of compounds of structural formula (VII):

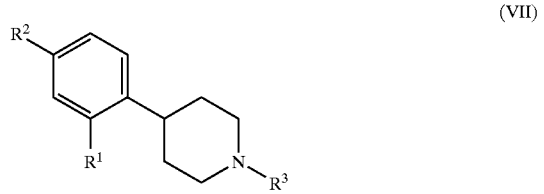

wherein
$R^1$ is selected from the group consisting of
  (1) CN,
  (2) C(O)OH,
  (3) C(O)—$C_{1-6}$ alkyl,
  (4) C(O$C_{1-6}$ alkyl)$_2$—$C_{1-6}$ alkyl, and
  (5) C($R^5$)$_2$N($R^5$)C(O)—$C_{1-6}$ alkyl;
each $R^2$ is independently selected from the group consisting of
  (1) hydrogen,
  (2) $C_{1-6}$ alkyl,
  (3) —(CH$_2$)$_n$-phenyl,
  (4) —(CH$_2$)$_n$-naphthyl,
  (5) —(CH$_2$)$_n$-heteroaryl,
  (6) —(CH$_2$)$_n$-heterocyclyl,
  (7) —(CH$_2$)$_n$$C_{3-7}$ cycloalkyl,
  (8) fluoride,
  (9) chloride,
  (10) O$R^5$,
  (11) —(CH$_2$)$_n$N($R^5$)$_2$,
  (12) —(CH$_2$)$_n$C≡N,
  (13) —(CH$_2$)$_n$CO$_2$$R^5$,
  (14) NO$_2$,
  (15) N($R^5$)$_2$,
  (16) —(CH$_2$)$_n$N$R^5$SO$_2$$R^5$,
  (17) —(CH$_2$)$_n$SO$_2$N($R^5$)$_2$,
  (18) —(CH$_2$)$_n$S(O)$_p$$R^5$,
  (19) —(CH$_2$)$_n$N$R^5$C(O)N($R^5$)$_2$,
  (20) —(CH$_2$)$_n$C(O)N($R^5$)$_2$,
  (21) —(CH$_2$)$_n$N$R^5$C(O)$R^5$,
  (22) —(CH$_2$)$_n$N$R^5$CO$_2$$R^5$,
  (23) —(CH$_2$)$_n$N$R^5$C(O)-heteroaryl,
  (24) —(CH$_2$)$_n$C(O)N$R^5$N($R^5$)$_2$,
  (25) —(CH$_2$)$_n$C(O)N$R^5$N$R^5$C(O)$R^5$,
  (26) O(CH$_2$)$_n$C(O)N($R^5$)$_2$,
  (27) CF$_3$,
  (28) CH$_2$CF$_3$,
  (29) OCF$_3$, and
  (30) OCH$_2$CF$_3$, wherein phenyl, naphthyl, heteroaryl, cycloalkyl, and heterocyclyl are unsubstituted or substituted with one to three substituents independently selected from halogen, hydroxy, oxo, $C_{1-4}$ alkyl, trifluoromethyl, and $C_{1-4}$ alkoxy, and wherein any methylene (CH$_2$) carbon atom in $R^2$ is unsubstituted or substituted with one to two groups independently selected from halogen, hydroxy, and $C_{1-4}$ alkyl, or two substituents when on the same methylene (CH$_2$) group are taken together with the carbon atom to which they are attached to form a cyclopropyl group;
$R^3$ is selected from the group consisting of
  (1) C(O)O-phenyl,
  (2) C(O)O—CH$_2$-phenyl,
  (3) C(O)O-isopropyl,
  (4) C(O)O-isobutyl, and
  (5) C(O)O-ethyl;
each $R^5$ is independently selected from the group consisting of
  (1) hydrogen,
  (2) $C_{1-6}$ alkyl,
  (3) —(CH$_2$)$_n$-phenyl,
  (4) —(CH$_2$)$_n$-heteroaryl,
  (5) —(CH$_2$)$_n$-naphthyl,
  (6) —(CH$_2$)$_n$-heterocyclyl,
  (7) —(CH$_2$)$_n$$C_{3-7}$ cycloalkyl, and
  (8) —(CH$_2$)$_n$$C_{3-7}$ bicycloalkyl, wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy, or two $R^5$ groups together with the atom to which they are attached form a 4- to 8-membered mono- or bicyclic ring system optionally containing an additional heteroatom selected from O, S, and $—NC_{1-4}$ alkyl.

comprising the steps of:
(a) preparing a compound of structural formula (IV):

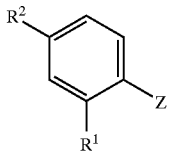

(IV)

wherein
$R^1$ and $R^2$ are as defined above, and Z is a halogen atom selected from the group consisting of bromide and iodide, by halogenating a compound of structural formula (III)

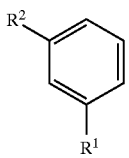

(III)

wherein
$R^1$ and $R^2$ are as defined above, and isolating the resulting product;
(b) forming an aryl magnesium halide of structural formula (V)

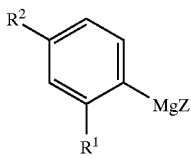

(V)

wherein $R^1$, $R^2$ and Z are as defined above, by treating the compound of structural formula (IV) with a magnesium compound;
(c) preparing a compound of structural formula (VI)

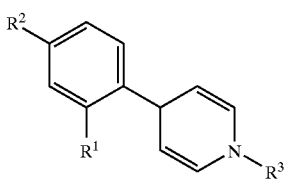

(VI)

wherein $R^1$, $R^2$ and $R^3$ are as defined above, by treating the aryl magnesium halide of structural formula (V)

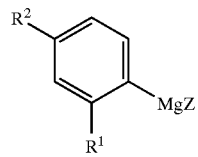

(V)

wherein $R^1$, $R^2$, and Z are as defined above, with a preformed pyridinium ion, and isolating the resulting product;
(d) reducing the dihydropyridine double bonds in the compound of structural formula (VI)

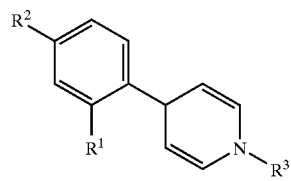

(VI)

wherein $R^1$, $R^2$ and $R^3$ are as defined above; and
(e) isolating the resulting product.

In one embodiment of the present invention, $R^1$ is CN.
In another embodiment of the present invention, $R^2$ is chloride.
In another embodiment of the present invention, $R^3$ is $C(O)O—CH_2$-phenyl.
In another embodiment of the present invention, Z is bromide. In a class of this embodiment, the compound of structural formula (III) in step (a) is brominated by treatment with a brominating agent in the presence of an acid. In a subclass of this class, the brominating agent is selected from the group consisting of 1,3-dibromo-5,5-dimethylhydantoin, $Br_2$, and N-bromosuccinimide. In a subclass of this subclass, the brominating agent is 1,3-dibromo-5,5-dimethylhydantoin. In another subclass of this class, the acid is selected from the group consisting of methanesulfonic acid, sulfuric acid, trifluoroacetic acid, and hydrochloric acid. In a subclass of this subclass, the acid is methanesulfonic acid. In yet another subclass of this class, the acid is trifluoroacetic acid and sulfuric acid.

In another embodiment of the present invention, the magnesium compound in step (b) is a compound of formula (IX)

$$R^a MgX,$$ (IX)

wherein $R^a$ is selected from the group consisting of isopropyl, cyclohexyl and tert-butyl, and X is selected from the group consisting of chloride, bromide, and iodide.

In a class of this embodiment, the magnesium compound of formula (X) is isopropyl magnesium chloride.
In another embodiment of the present invention, the magnesium compound in step (b) is magnesium.
In another embodiment of the present invention, the pyridinium ion in step (c) is formed by treating pyridine, with a chloroformate of formula (X)

$$ClC(O)OR^b,$$ (X)

wherein R^b is selected from the group consisting of ethyl, isopropyl, isobutyl, phenyl and benzyl, in the presence of a copper compound. In a class of this embodiment, the copper compound is selected from the group consisting of copper iodide, BuCu, BuCu—BF$_3$, and CuBr. In another class of this embodiment, the copper compound is copper iodide. In another class of this embodiment, the chloroformate of formula (X) is benzyl chloroformate.

In another embodiment of the present invention, the dihydropyridine double bonds of compound (VI) are reduced by hydrogenation in the presence of a catalyst. In a class of this embodiment, the catalyst is selected from the group consisting of RhCl(PPh$_3$)$_3$, Pd/C, PtO$_2$, Pt/C, and Rh/C. In a subclass of this class, the catalyst is RhCl(PPh$_3$)$_3$. In another class of this embodiment, the hydrogenation is run in a hydrogen atmosphere at a hydrogen pressure of about 40 psi to about 100 psi. In a subclass of this class, the hydrogenation is run at a hydrogen pressure of about 40 psi.

In another embodiment, the process further comprises the steps of
(a) cleaving the R$^3$ protecting in the compound of structural formula (VII)

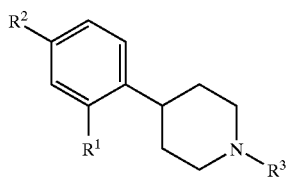

(VII)

wherein R$^1$, R$^2$, and R$^3$ are as defined supra,
to afford a compound of structural formula (VIII)

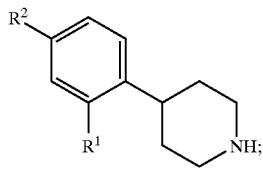

(VIII)

(b) isolating the resulting product.
In a class of this embodiment, R$^1$ is CN.
In another class of this embodiment, R$^2$ is chloride.
In yet another class of this embodiment, R$^3$ is C(O)O—CH$_2$-phenyl.

In another embodiment, the process further comprises the steps of
(a) cleaving the R$^3$ protecting group in the compound of structural formula (VII)

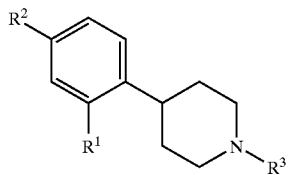

(VII)

wherein R$^1$, R$^2$, and R$^3$ are as defined supra,
to afford a compound of structural formula (VIII)

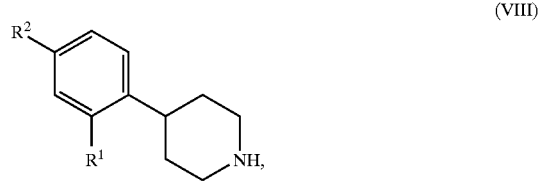

(VIII)

and isolating the resulting product;
(b) adding a R$^4$ protecting group to the free amine (VIII) to form the compound of structural formula (I),

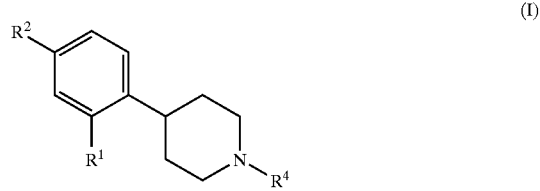

(I)

wherein R$^1$, R$^2$ are as defined above, and
R$^4$ is selected from the group consisting of
(1) C(O)O-tert-butyl,
(2) C(O)O—CH$_2$-phenyl, and
(3) C(O)O-phenyl;
(c) isolating the resulting product.
In a class of this embodiment, R$^1$ is CN.
In another class of this embodiment, R$^2$ is chloride.
In another class of this embodiment, R$^3$ is C(O)O—CH$_2$-phenyl.
In yet another class of this embodiment, R$^4$ is C(O)O-tert-butyl.

The present invention also provides a process for the preparation of compounds of structural formula (I):

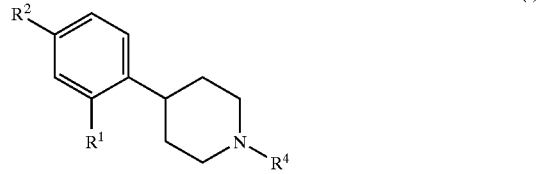

(I)

wherein
R$^1$ is selected from the group consisting of
(1) CN,
(2) C(O)OH,
(3) C(O)—C$_{1-6}$ alkyl,
(4) C(OC$_{1-6}$ alkyl)$_2$—C$_{1-6}$ alkyl, and
(5) C(R$^5$)$_2$N(R$^5$)C(O)—C$_{1-6}$ alkyl;
each R$^2$ is independently selected from the group consisting of
(1) hydrogen,
(2) C$_{1-6}$ alkyl,
(3) —(CH$_2$)$_n$-phenyl,
(4) —(CH$_2$)$_n$-naphthyl,
(5) —(CH$_2$)$_n$-heteroaryl, (6) —(CH$_2$)$_n$-heterocyclyl,
(7) —(CH$_2$)$_n$C$_{3-7}$ cycloalkyl,
(8) fluoride,
(9) chloride,
(10) OR$^5$,
(11) —(CH$_2$)$_n$N(R$^5$)$_2$,
(12) —(CH$_2$)$_n$C≡N,
(13) —(CH$_2$)$_n$CO$_2$R$^5$,
(14) NO$_2$,
(15) N(R$^5$)$_2$,
(16) —(CH$_2$)$_n$NR$^5$SO$_2$R$^5$,
(17) —(CH$_2$)$_n$SO$_2$N(R$^5$)$_2$,
(18) —(CH$_2$)$_n$S(O)$_p$R$^5$,
(19) —(CH$_2$)$_n$NR$^5$C(O)N(R$^5$)$_2$,
(20) —(CH$_2$)$_n$C(O)N(R$^5$)$_2$,
(21) —(CH$_2$)$_n$NR$^5$C(O)R$^5$,
(22) —(CH$_2$)$_n$NR$^5$CO$_2$R$^5$,
(23) —(CH$_2$)$_n$NR$^5$C(O)-heteroaryl,
(24) —(CH$_2$)$_n$C(O)NR$^5$N(R$^5$)$_2$,
(25) —(CH$_2$)$_n$C(O)NR$^5$NR$^5$C(O)R$^5$,
(26) O(CH$_2$)$_n$C(O)N(R$^5$)$_2$,
(27) CF$_3$,
(28) CH$_2$CF$_3$,
(29) OCF$_3$, and
(30) OCH$_2$CF$_3$, wherein phenyl, naphthyl, heteroaryl, cycloalkyl, and heterocyclyl are unsubstituted or substituted with one to three substituents independently selected from halogen, hydroxy, oxo, C$_{1-4}$ alkyl, trifluoromethyl, and C$_{1-4}$ alkoxy, and wherein any methylene (CH$_2$) carbon atom in R$^2$ is unsubstituted or substituted with one to two groups independently selected from halogen, hydroxy, and C$_{1-4}$ alkyl, or two substituents when on the same methylene (CH$_2$) group are taken together with the carbon atom to which they are attached to form a cyclopropyl group;

R$^4$ is selected from the group consisting of
(1) C(O)O-tert-butyl,
(2) C(O)O—CH$_2$-phenyl, and
(3) C(O)O-phenyl; and each R$^5$ is independently selected from the group consisting of
(1) hydrogen,
(2) C$_{1-6}$ alkyl,
(3) —(CH$_2$)$_n$-phenyl,
(4) —(CH$_2$)$_n$-heteroaryl,
(5) —(CH$_2$)$_n$-naphthyl,
(6) —(CH$_2$)$_n$-heterocyclyl,
(7) —(CH$_2$)$_n$C$_{3-7}$ cycloalkyl, and
(8) —(CH$_2$)$_n$C$_{3-7}$ bicycloalkyl, wherein alkyl, phenyl, heteroaryl, heterocyclyl, and cycloalkyl are unsubstituted or substituted with one to three groups independently selected from halogen, C$_{1-4}$ alkyl, hydroxy, and C$_{1-4}$ alkoxy, or two R$^5$ groups together with the atom to which they are attached form a 4- to 8-membered mono- or bicyclic ring system optionally containing an additional heteroatom selected from O, S, and —NC$_{1-4}$ alkyl;

comprising the steps of:
(a) preparing a compound of structural formula (IV):

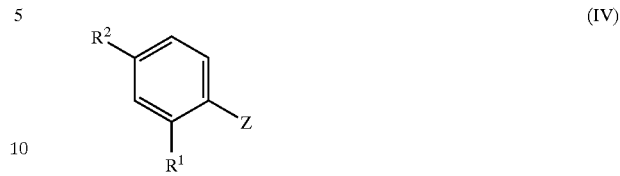

(IV)

wherein
R$^1$ and R$^2$ are as defined above, and Z is a halogen atom selected from the group consisting of bromide and iodide,
by halogenating a compound of structural formula (III)

(III)

wherein
R$^1$ and R$^2$ are as defined above, and isolating the resulting product;
(b) forming an aryl magnesium halide of structural formula (V)

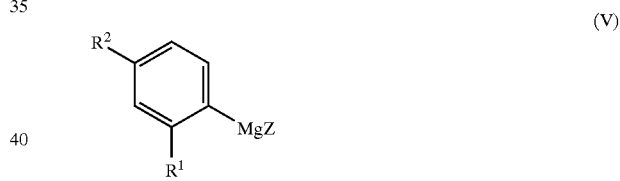

(V)

wherein R$^1$, R$^2$ and Z are as defined above,
by treating the compound of structural formula (IV) with a magnesium compound;
(c) preparing a compound of structural formula (VI)

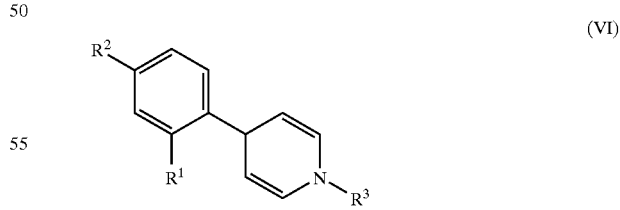

(VI)

wherein R$^1$ and, R$^2$ are as defined above, and
R$^3$ is selected from the group consisting of
(1) C(O)O-phenyl,
(2) C(O)O—CH$_2$-phenyl,
(3) C(O)O-isopropyl,
(4) C(O)O-isobutyl, and
(5) C(O)O-ethyl, by treating the aryl magnesium halide of structural formula (V)

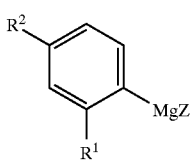

wherein $R^1$, $R^2$, and Z are as defined above, with a preformed pyridinium ion, and isolating the resulting product;
(d) reducing the dihydropyridine double bonds in the compound of structural formula (VI)

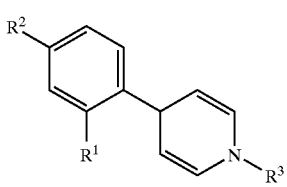

wherein $R^1$, $R^2$ and $R^3$ are as defined above; and
(e) isolating the resulting product.

In one embodiment of the present invention, $R^1$ is CN.

In another embodiment of the present invention, $R^2$ is chloride.

In another embodiment of the present invention, $R^3$ is $C(O)O$—$CH_2$-phenyl.

In another embodiment of the present invention, $R^4$ is $C(O)O$-tert-butyl.

In another embodiment of the present invention, Z is bromide. In a class of this embodiment, the compound of structural formula (III) in step (a) is brominated by treatment with a brominating agent in the presence of an acid. In a subclass of this class, the brominating agent is selected from the group consisting of 1,3-dibromo-5,5-dimethylhydantoin, $Br_2$, and N-bromosuccinimide. In a subclass of this subclass, the brominating agent is 1,3-dibromo-5,5-dimethylhydantoin. In another subclass of this class, the acid is selected from the group consisting of methanesulfonic acid, sulfuric acid, trifluoroacetic acid, and hydrochloric acid. In a subclass of this subclass, the acid is methanesulfonic acid. In yet another subclass of this subclass, the acid is trifluoroacetic acid and sulfuric acid.

In another embodiment of the present invention, the magnesium compound in step (b) is a compound of formula (IX)

$$R^a MgX, \quad (IX)$$

wherein $R^a$ is selected from the group consisting of isopropyl, cyclohexyl and tert-butyl, and X is selected from the group consisting of chloride, bromide, and iodide.

In a class of this embodiment, the magnesium compound of formula (X) is isopropyl magnesium chloride.

In another embodiment of the present invention, the magnesium compound is magnesium.

In another embodiment of the present invention, the pyridinium ion in step (c) is formed by treating pyridine, with a chloroformate of formula (X)

$$ClC(O)OR^b, \quad (X)$$

wherein $R^b$ is selected from the group consisting of ethyl, isopropyl, isobutyl, phenyl and benzyl, in the presence of a copper compound. In a class of this embodiment, the copper compound is selected from the group consisting of copper iodide, BuCu, BuCu—$BF_3$, and CuBr. In another class of this embodiment, the copper compound is copper iodide. In another class of this embodiment, the chloroformate of formula (X) is benzyl chloroformate.

In another embodiment of the present invention, the dihydropyridine double bonds of compound (VI) are reduced by hydrogenation in the presence of a catalyst and an anhydride. In a class of this embodiment, the catalyst is selected from the group consisting of Pd/C, $PtO_2$, and Pt/C. In a subclass of this class, the catalyst is Pd/C. In another class of this embodiment, the anhydride is selected from the group consisting of tert-butyloxycarbonyl anhydride, dibenzyl dicarbonate, and benzoic anhydride. In a subclass of this class, the anhydride is tert-butyloxycarbonyl anhydride. In another class of this embodiment, the hydrogenation is run in a hydrogen atmosphere at a hydrogen pressure of about 40 psi to about 100 psi. In a subclass of this class, the hydrogenation is run at a hydrogen pressure of about 70 psi, and at a temperature of about 45° C.

The present invention also provides a process for the preparation of compounds of structural formula (I):

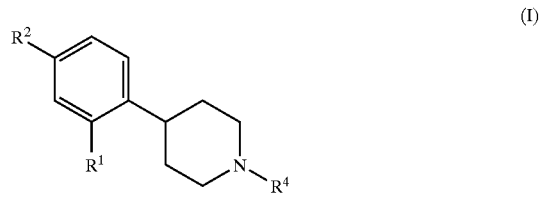

wherein
$R^1$ is selected from the group consisting of
(1) CN,
(2) C(O)OH,
(3) C(O)—$C_{1-6}$ alkyl,
(4) $C(OC_{1-6}$ alkyl$)_2$—$C_{1-6}$ alkyl, and
(5) $C(R^5)_2N(R^5)C(O)$—$C_{1-6}$ alkyl;
each $R^2$ is independently selected from the group consisting of
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_n$-heterocyclyl,
(7) —$(CH_2)_nC_{3-7}$ cycloalkyl,
(8) fluoride,
(9) chloride,
(10) $OR^5$,
(11) —$(CH_2)_nN(R^5)_2$,
(12) —$(CH_2)_nC\equiv N$,
(13) —$(CH_2)_nCO_2R^5$,
(14) $NO_2$,
(15) $N(R^5)_2$,
(16) —$(CH_2)_nNR^5SO_2R^5$,
(17) —$(CH_2)_nSO_2N(R^5)_2$,
(18) —$(CH_2)_nS(O)_pR^5$,
(19) —$(CH_2)_nNR^5C(O)N(R^5)_2$,
(20) —$(CH_2)_nC(O)N(R^5)_2$,
(21) —$(CH_2)_nNR^5C(O)R^5$,

(22) —(CH$_2$)$_n$NR$^5$CO$_2$R$^5$,
(23) —(CH$_2$)$_n$NR$^5$C(O)-heteroaryl,
(24) —(CH$_2$)$_n$C(O)NR$^5$N(R$^5$)$_2$,
(25) —(CH$_2$)$_n$C(O)NR$^5$NR$^5$C(O)R$^5$,
(26) O(CH$_2$)$_n$C(O)N(R$^5$)$_2$,
(27) CF$_3$,
(28) CH$_2$CF$_3$,
(29) OCF$_3$, and
(30) OCH$_2$CF$_3$, wherein phenyl, naphthyl, heteroaryl, cycloalkyl, and heterocyclyl are unsubstituted or substituted with one to three substituents independently selected from halogen, hydroxy, oxo, C$_{1-4}$ alkyl, trifluoromethyl, and C$_{1-4}$ alkoxy, and wherein any methylene (CH$_2$) carbon atom in R$^2$ is unsubstituted or substituted with one to two groups independently selected from halogen, hydroxy, and C$_{1-4}$ alkyl, or two substituents when on the same methylene (CH$_2$) group are taken together with the carbon atom to which they are attached to form a cyclopropyl group;

R$^4$ is selected from the group consisting of
(1) C(O)O-tert-butyl,
(2) C(O)O—CH$_2$-phenyl, and
(3) C(O)O-phenyl; and each R$^5$ is independently selected from the group consisting of
(1) hydrogen,
(2) C$_{1-6}$ alkyl,
(3) —(CH$_2$)$_n$-phenyl,
(4) —(CH$_2$)$_n$-heteroaryl,
(5) —(CH$_2$)$_n$-naphthyl,
(6) —(CH$_2$)$_n$-heterocyclyl,
(7) —(CH$_2$)$_n$C$_{3-7}$ cycloalkyl, and
(8) —(CH$_2$)$_n$C$_{3-7}$ bicycloalkyl, wherein alkyl, phenyl, heteroaryl, heterocyclyl, and cycloalkyl are unsubstituted or substituted with one to three groups independently selected from halogen, C$_{1-4}$ alkyl, hydroxy, and C$_{1-4}$ alkoxy, or two R$^5$ groups together with the atom to which they are attached form a 4- to 8-membered mono- or bicyclic ring system optionally containing an additional heteroatom selected from O, S, and —NC$_{1-4}$ alkyl;

comprising the steps of:
(a) reducing the dihydropyridine double bonds in the compound of structural formula (VI)

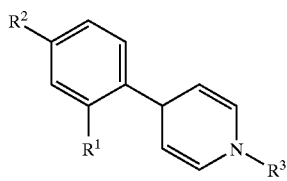
(VI)

wherein R$^1$ and, R$^2$ are as defined above, and R$^3$ is selected from the group consisting of
(1) C(O)O-phenyl,
(2) C(O)O—CH$_2$-phenyl,
(3) C(O)O-isopropyl,
(4) C(O)O-isobutyl, and
(5) C(O)O-ethyl,
(b) isolating the resulting product.

In one embodiment of the present invention, R$^1$ is CN.
In another embodiment of the present invention, R$^2$ is chloride.
In another embodiment of the present invention, R$^3$ is C(O)O—CH$_2$-phenyl.

In another embodiment of the present invention, R$^4$ is C(O)O-tert-butyl.

In another embodiment of the present invention, the dihydropyridine double bonds of compound (VI) are reduced by hydrogenation in the presence of a catalyst and an anhydride. In a class of this embodiment, the catalyst is selected from the group consisting of Pd/C, PtO$_2$, and Pt/C. In a subclass of this class, the catalyst is Pd/C. In another class of this embodiment, the anhydride is selected from the group consisting of tert-butyloxycarbonyl anhydride, dibenzyl dicarbonate, and benzoic anhydride. In a subclass of this class, the anhydride is tert-butyloxycarbonyl anhydride. In another class of this embodiment, the hydrogenation is run in a hydrogen atmosphere at a hydrogen pressure of about 40 psi to about 100 psi. In a subclass of this class, the hydrogenation is run at a hydrogen pressure of about 70 psi, and at a temperature of about 45° C.

A further embodiment of this invention comprises the novel compound 1-5

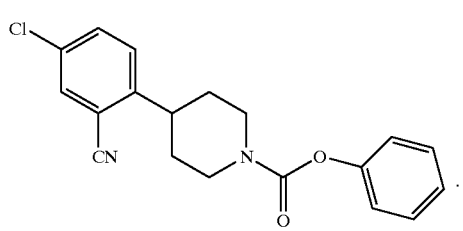
1-5

A further embodiment of this invention comprises the novel compound 1-6

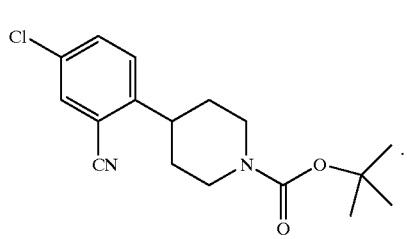
1-6

Further embodiments of this invention comprise the following novel compounds which are intermediates in the preparation of 1-6 and other compounds of structural formula (I):

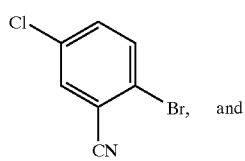
1-2 and

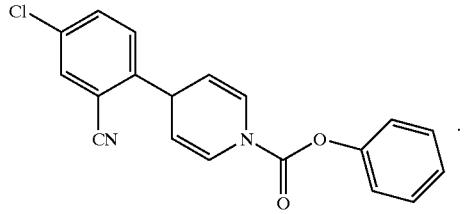
1-4

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" represents a monocyclic heteroaromatic ring; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, NR$^4$R$^4$ may represent NH$_2$, NHCH$_3$, N(CH$_3$)CH$_2$CH$_3$, and the like.

The process and intermediates can be exemplified with the preparation of 4-(4-Chloro-2-cyanophenyl)piperidine-1-carboxylic acid tert-butyl ester (1-6) as shown in Scheme 1.

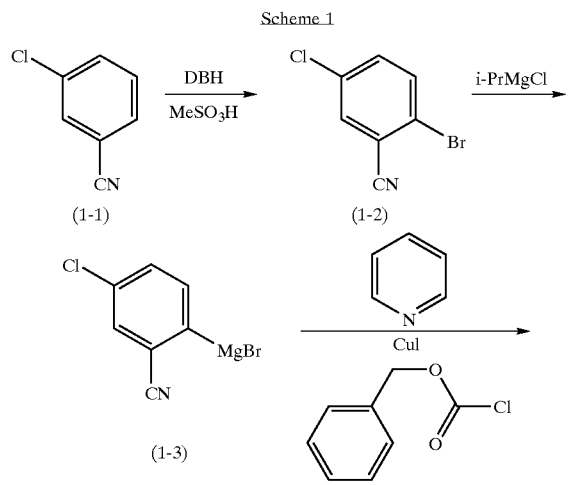

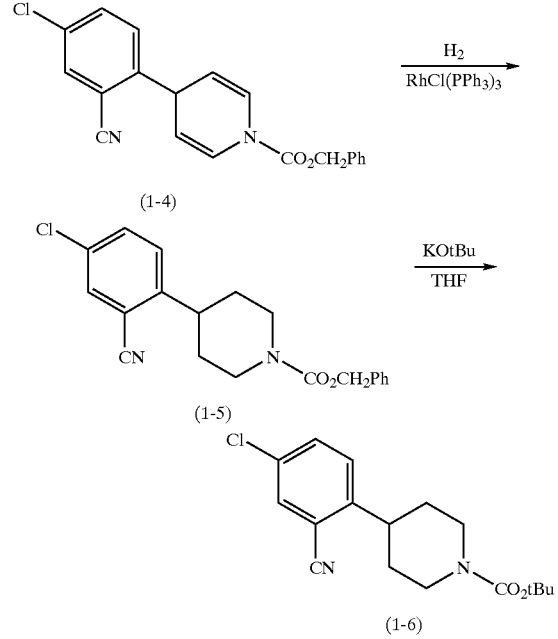

As shown in Scheme 1, the known 2-bromo-5-chlorobenzonitrile 1-2 is prepared by treatment of 3-chlorobenzonitrile 1-1 with 1,3-dibromo-5,5-dimethylhydantoin in the presence of an acid, such as methanesulfonic acid, sulfuric acid, trifluoroacetic acid, or hydrochloric acid, in an aprotic solvent such as cyclohexane, dichloro-methane, or dichloroethane, at a temperature of about 20° C. to about 30° C. After aging for about 1 to 2 hours, the final product 1-2 is isolated.

Other reagents may also be employed to brominate 1-1, such as bromine in the presence of a catalyst such as a Lewis acid or N-bromosuccinimide. Iodination may be affected by treating 3-chlorobenzonitrile 1-1 with iodine in the presence of a catalyst such as ICl, or N-iodosuccinimide.

Compound 1-4 was prepared by treating the aryl magnesium bromide intermediate 1-3 with a preformed acyl pyridinium ion.

The aryl magnesium bromide 1-3 was formed by treating the bromide 1-2 with an alkyl magnesium halide, such as isopropyl magnesium chloride, cyclohexyl magnesium chloride, or t-butyl magnesium chloride, in an aprotic solvent such as THF, MTBE, or toluene, at a temperature of about −10° C. to about −20° C. The aryl magnesium bromide 1-3 may also be formed by treating bromide 1-2 with magnesium. Alkyl magnesium iodides may also be used in this reaction.

The acyl pyridinium ion was prepared using Comins' methodology by treating pyridine with benzyl chloroformate in the presence of copper iodide in an aprotic solvent such as THF, ether, or toluene, at a temperature of about −20° C. to about 0° C. Other chloroformates may be used for the formation of the acyl pyridinium ion, including but not limited to, ethyl chloroformate, isopropyl chloroformate, isobutyl chloroformate, and phenyl chloroformate. Other copper compounds may also be used as catalysts for the acyl pyridinium ion formation, such as BuCu, BuCu—BF$_3$, and CuBr.

The aryl magnesium bromide 1-3 was slowly added to the preformed acyl pyridinium ion, maintaining the reaction temperature below about 0° C. The reaction was aged at 0° C. until completion, and the CBZ protected dihyropyridine 1-4 was isolated.

Piperidine 1-5 is prepared by treating the dihydropyridine 1-4 in a solvent, such as toluene or a lower alkanol, for example, methanol or ethanol, with hydrogen gas under medium to high pressure, such as 40 psi to 100 psi, in the presence of a RhCl(PPh$_3$)$_3$ catalyst until hydrogen uptake ceases. Other catalysts which can be employed in the hydrogenation reaction include Raney nickel, Pd/C, Pd(OH)$_2$, Rh/C, Ru/C, Pd/Al$_2$O$_3$, Pd(CaCO$_3$), Pd(BaSO$_4$), Pt/C, PtO$_2$, Pt/Al$_2$O$_3$, Rh/Al$_2$O$_3$, and Ru/Al$_2$O$_3$. Other solvents that may be used include toluene, toluene/ethanol, ethyl acetate, isopropyl alcohol, tert-butanol-THF, methanol-acetic acid and THF.

Boc protected piperidine 1-6 is prepared by treating with CBZ protected piperidine 1-5 in an aprotic solvent, such as THF or hexanes, with potassium tert-butoxide at a temperature of about 45° C. until completion, followed by quenching and working up the reaction, and isolating the final product 1-6.

The CBZ protecting group of compound 1-5 may also be cleaved to give the free amine, which may be re-protected with another amine protecting group using standard conditions. Standard conditions required to remove protecting groups are found in textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their addition and removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide.

Alternatively, as shown in Scheme 2, the CBZ protected dihydropyridine 1-4 may be converted directly to the BOC protected piperidine 1-6. By reducing the dihydropyridine ring by hydrogenation in the presence of a catalyst and an anhydride.

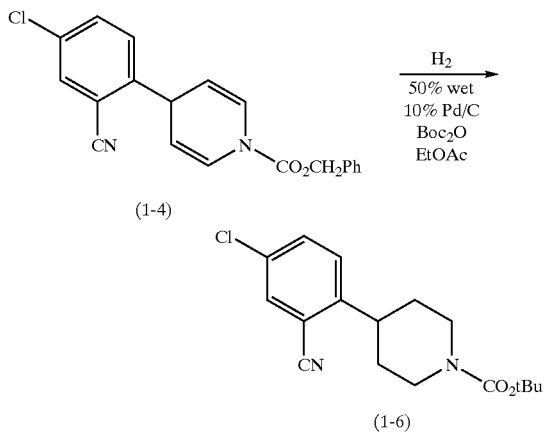

Scheme 2

Catalysts which may be useful to hydrogenate the dihydropyridine double bonds, as shown in Scheme 2, include, but are not limited to, PtO$_2$, Pd/C, and Pt/C. The hydrogenation may be run in a hydrogen atmosphere under 40 psi to 100 psi of hydrogen gas. In particular, the hydrogenation may be run in a hydrogen atmosphere under 70 psi of hydrogen gas at a temperature of about 45° C. This reaction may also be run in the presence of other anhydrides, including, but not limited to, benzoic anhydride and dibenzyl dicarbonate.

Abbreviations Used in the Description of the Preparation of the Compounds of the Present Invention:

BOC (Boc) is tert-butyloxycarbonyl; Boc$_2$O is Boc anhydride; Boc anhydride is tert-butyloxycarbonyl anhydride; Bu is butyl; CBZ is benzyloxy-carbonyl; Cu is copper; CuI is copper (I) iodide; DBH is 1,3-dibromo-5,5-dimethylhydantoin; EtOAc is ethyl acetate; equiv is equivalents; g is grams; h or hr is hour(s); H$_2$ is hydrogen; HCl is hydrochloric acid, HPLC is high pressure liquid chromatography; mm Hg is millimeters of mercury; kg is kilograms; L is liters; M is molar; mL is milliliters; MeOH is methanol, mol is moles; MTBE is methyl t-butyl ether; N is normal; NMP is N-methyl pyrrolidinone; NaCl is sodium chloride; NaOH is sodium hydroxide; NMR is nuclear magnetic resonance; Ph (ph) is phenyl; psi is pounds per square inch; PPh3 is triphenyl phosphine; and THF is tetrahydrofuran.

The following Example is provided to illustrate the invention and is not to be construed as limiting the scope of the invention in any manner. A representative experimental procedure utilizing the novel process is detailed below. For purposes of illustration, the following Example is directed to the preparation of compounds 1-5 and 1-6, but doing so is not intended to limit the present invention to a process for making those specific compounds.

EXAMPLE 1

4-(4-Chloro-2-cyanophenyl)piperidine-1-carboxylic Acid Tert-butyl Ester (1-6)

Step A: Preparation of Compound 1-2

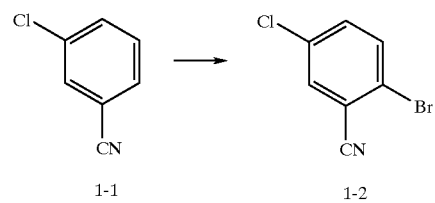

To a 400 L glass lined vessel was charged 1,3-dibromo-5,5-dimethyl-hydantoin (DBH) (10.88 kg, 38.6 mol), followed by methane sulfonic acid (111.4 kg). The resulting slurry was warmed to 35° C. to form a DBH solution.

To a separate 400 L vessel was charged 3-chlorobenzonitrile 1-1 (8.050 kg, 58.5 mol, Acros, Lancaster) melt and cyclohexane (1.8 L total), followed by methanesulfonic acid (47.6 kg) to form a benzonitrile solution, which was warmed to 25–30° C. to dissolve any solids. The DBH solution was added to the benzonitrile solution over a period of about 30 minutes with fast agitation while maintaining a batch temperature of <30° C. The empty DBH solution containing vessel was rinsed with methane sulfonic acid (5.0 kg) and the rinse was added to the reaction mixture. The reaction was aged at 30° C. for 1 to 2 hours to affect reaction conversion >95 area % (tracked via HPLC assay). The reaction was then cooled to about 14° C. and slowly quenched with water (80.5 L) to maintain a temperature of <30° C. The reaction was then re-cooled to 20° C. and MTBE was added (208.5 kg) at <30° C. under agitation. The mixture was allowed to settle, the layers were separated and the aqueous layer was extracted with 101 kg of MTBE at 30° C., followed by 30 kg of MTBE. The organic layers were combined and washed with 50 kg 1.6 N NaOH, and 54 kg water, and then concentrated to 48 L, cooled and seeded (10 g of seed). Once a slurry formed, the concentration was resumed until a batch volume of 40 L was achieved. The resulting slurry was aged at 20° C. for 1.5 hours and then filtered. The cake was washed with 12 kg of 1:1 MTBE:cyclohexane (in 2 drops). The wet solids were dried in a filter dryer to give 1-2. $^1$H NMR (CDCl$_3$, 400 MHz) δ 7.39 (d, J=2.2 Hz, 1H), 7.22 (dd, J=2.3, 8.4 Hz, 1H), 7.16 (d, J=8.5 Hz, 1H).

An alternative synthesis of compound 1-2 follows: To a solution of 3-chlorobenzonitrile 1-1 (50 g, 360 mmol) in trifluoroacetic acid (180 mL) was added sulfuric acid (24 mL) and then 1,3-dibromo-5,5-dimethylhydantoin (67 g, 234 mmol) in portions over 8 minutes. The reaction temperature was allowed to reach 31° C. and then cooling was applied to bring the temperature to 24° C. After a 6 hour age, the heterogeneous reaction was cooled to 10° C. and water (250 mL) was added. Following a 10 minute age, the reaction was filtered and the product cake was washed twice with water (250 and 100 mL) to afford a white solid (52.4 g, 63%). $^1$H NMR (CDCl$_3$, 400 MHz) δ 7.64–7.62 (m, 2H), 7.44 (dd, J=8.6, 2.5 Hz, 1H); $^{13}$C NMR (CDCl$_3$, 100 MHz) δ134.2, 134.1, 133.9, 133.8, 123.3, 117.2, 115.8.

Step B: Preparation of Compound 1-4

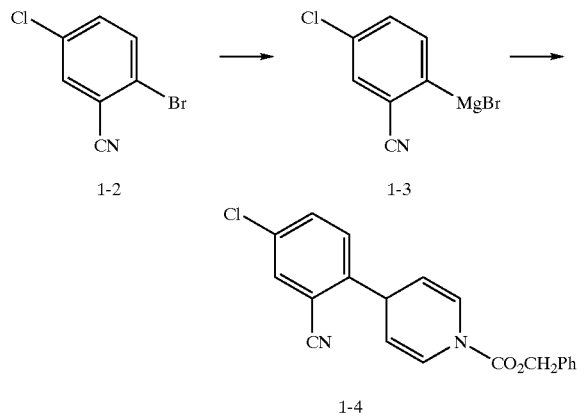

To a 150 L glass lined reactor equipped with an overhead stirrer, dropping funnel, nitrogen blanket, and thermal couple readout was charged 2-bromo-5-chlorobenzonitrile 1-2 (4.98 kg, 23.0 moles), followed by 100 L of THF. The resulting solution was cooled to −35° C. using direct injection of dry liquid nitrogen. To this solution was added isopropyl magnesium chloride (21.3 kg, 22.7 L, Chemetall), keeping internal temperature less than −22° C., to form the Grignard reagent 1-3. The resulting solution was stirred until the formation of the Grignard reagent 1-3 was complete as determined by HPLC analysis. To an adjacent 400 L reactor, equipped with an overhead stirrer, nitrogen blanket, and thermal couple readout, was added THF (100 L) and copper iodide (219 g). The resulting solution was cooled to −10° C., and pyridine (2 equivalents, 3.64 kg, 3.72 L) was added. To this solution was added dropwise benzyl chloroformate (1.2 equivalents, 6.08 kg, 4.87 L), keeping the internal tempera- ture at <0° C., to form a heterogenous mixture. To this heterogenous mixture was added the previously formed Grignard reagent 1-3 over 30 minutes by nitrogen pressure, while keeping the internal temperature at <5° C. The resulting solution was aged at 0° C. for 30 minutes (HPLC analysis at this point showed 1.1 A % starting material), and then quenched by the addition of 10% aqueous ammonium chloride (50 L), followed by the addition of 50 L MTBE. The resulting mixture was allowed to settle, and the resulting aqueous layer was removed. The organic layer was washed successively with 50 L 10% aqueous ammonium chloride, 50 L to 75 L of 1 N HCl, 50 L of 10% NaHCO$_3$, and 50 L of 5% NaCl. The resulting organic layer was concentrated under reduced pressure to about 100 L (first 75 L of distillate was removed at atmospheric pressure and partial vacuum then introduced), then 100 L of MeOH was added via slow bleed while the distillation continued. The resulting mixture was concentrated to 100 L, and seeded (50 g of seed); the distillation continued to a final volume of 60 L. The mixture was then cooled to 0° C. and filtered to give a crude solid, which was washed with 15 L of methanol and allowed to dry under nitrogen. The solid was then distributed in stainless steel trays and vacuum dried in an oven (120–160 mmHg, 40° C.) to give 1-4. $^1$H NMR (CDCl$_3$, 400 MHz) 7.82–7.50 (m, 2H), 7.44–7.34 (m, 6H), 6.95–6.85 (br m, 2H), 5.27 (s, 2H), 4.97–4.89 (m, 2H), 4.65–4.63 (m, 1H).

Step C: Preparation of Compound 1-5

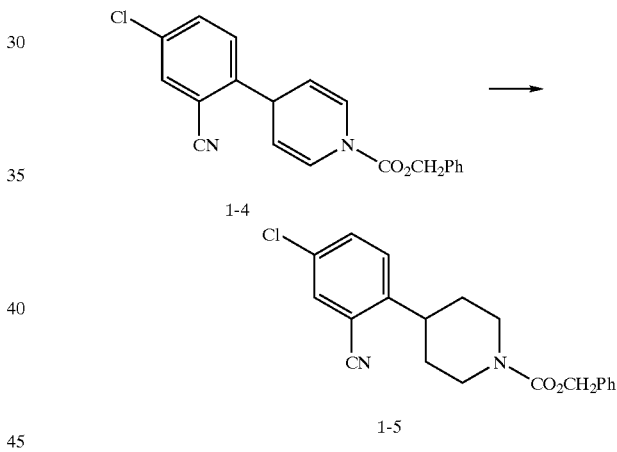

A 150 L reactor was charged with dihydropyridine 1-4 (9.18 kg, 27.2 mol) followed by toluene (55.3 kg) and RhCl(PPh$_3$)$_3$ (Wilkinsons catalyst, 2.419 kg, 2.5 mol in 20 kg of toluene, followed by a second 20 kg toluene rinse). The resultant slurry was warmed to and aged at +75° C. under 40 psi H$_2$ for 5.5 hours or until the reaction was complete (monitored via HPLC). Following oxidation of the triphenylphosphine, the reaction stream was filtered through a plug of SiO$_2$ (27.5 kg), and rinsed with 10% EtOAc/toluene (84 L). The solution was solvent switched to toluene and concentrated until a final volume of 18 L was reached. The solution was allowed to cool to 20° C. and heptane (7.5 kg) was slowly charged. The solution was seeded, and the resulting slurry was allowed to cool to room temperature and aged overnight. Additional heptane (41.8 kg) was added slowly over 2 hours. The resulting slurry was cooled to 0° C., filtered, and the filter cake was washed with 1:4 toluene:heptane (12 L). The filter cake was then transferred to stainless steel trays and dried in a vacuum oven at a temperature of about 25° C. to 28° C. for 12 hours to give 1-5. $^1$H NMR (CDCl$_3$, 400 MHz) δ 7.64 (s, 1H), 7.58–7.56 (m, 1H), 7.40–7.33 (m, 3H), 7.24–7.20 (m, 1H), 7.15–7.13

(m, 2H), 4.49 (br s, 2 H), 3.28–3.22 (m, 3H), 1.98–1.94 (m, 2H), 1.76 (app qd, J=12.7, 4.0 Hz, 2H).

Step D: Preparation of Compound 1-6

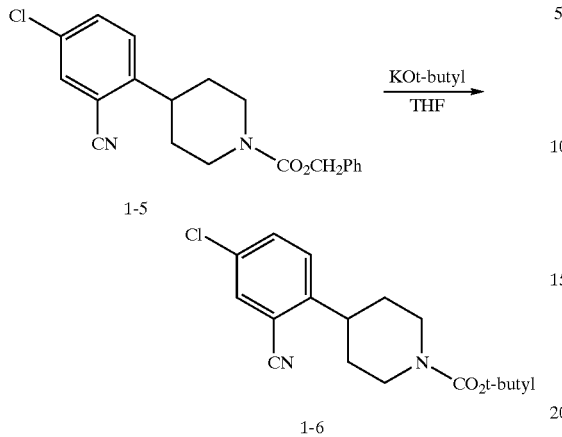

A 100 L flask was charged with hexanes (3 L) and the CBZ-protected piperidine 1-5 (3.265 kg), followed by THF (3 L). Potassium t-butoxide (28L, 1.0M in THF) was then added to the vessel, and the resulting homogeneous reaction solution heated to 40–45° C., and aged about 3 to 4 hours, or until the reaction was complete. The reaction mixture was cooled to 5° C., and water (14 L) was added, followed by the addition of hexanes (28 L). The resulting mixture was stirred for 30 minutes and allowed to settle. The lower aqueous layer was cut away and the remaining organic layer was washed twice with water (2×24 L). The organic layer was then treated with Ecosorb C-941™ (1.14 kg), and the resulting mixture was stirred overnight at ambient temperature. The mixture was then filtered through Solka Floc™, and the resulting filter cake was washed with hexanes (3 L). The resulting solution was solvent switched, under vacuum, to ethanol so that the concentration of product in solution was 190–200 g/L (approximately 14 L), and water (4.5 L) was slowly added to give a slurry. The thin slurry was cooled to −10° C., and aged at −10° C. until the supernatant was below 15 g/L, then the solids were filtered on a filter pot. The filter cake was washed with cold, 2:1 ethanol/water, and dried at 40° C. under vacuum to give 1-6. $^1$H NMR (CDCl$_3$, 400 MHz): δ 7.61 (d, J=2.4, 1H), 7.53 (dd, J=8.4, 2.4, 1H), 7.29 (d, J=8.4, 1H), 4.28 (br. d, approx. 10,2H), 3.11 (tt, J=12.0, 3.6, 1H), 2.87 (br. t, J approx. 12, 2H), 1.85 (m, 2H), 1.61 (m, 2H), 1.49 (s, 9H).

Alternatively, 4-(4-Chloro-2-cyanophenyl)piperidine-1-carboxylic acid tert-butyl ester 1-6 may be prepared from compound 1-4 as shown in Example 2.

EXAMPLE 2

4-(4-Chloro-2-cyanophenyl)piperidine-1-carboxylic Acid Tert-butyl Ester (1-6)

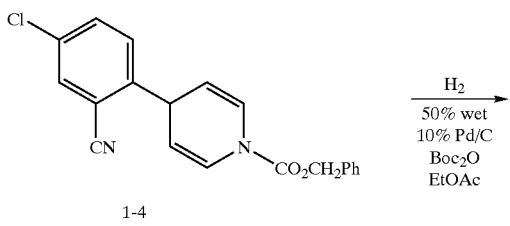

-continued

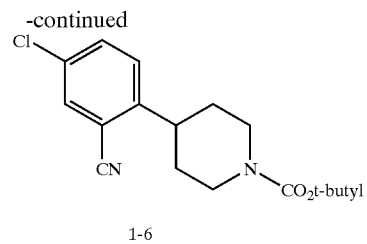

A 100 mL bottle was charged with the CBZ protected-dihydropyridine 1-4 (5.0 g, 14.2 mmol) followed by EtOAc (150 mL) and Boc$_2$O (3.4 g, 15.5 mol) to form a slurry. The resulting slurry was warmed gently and agitated to form a homogeneous solution. 50% wet 10% Pd/C catalyst (0.78 g, 15.6%) was added to the dihydropyridine solution and the mixture was aged at 45° C. under 70 psi of H$_2$ for 8 hours. Upon completion of the reaction, the solution was filtered through Solka Floc™ and solvent switched to MeOH. Upon addition of 2:1 MeOH—H$_2$O, compound 1-6 precipitated as a solid. After stirring overnight at room temperature, the solution was filtered to give the tert-butoxy protected piperidine 1-6 as a solid. The solid may be recrystallized with heptane to increase purity. $^1$H NMR (CDCl$_3$, 400 MHz): δ 7.61 (d, J=2.4, 1H), 7.53 (dd, J=8.4, 2.4, 1H), 7.29 (d, J=8.4, 1H), 4.28 (br. d, J approx. 10, 2H), 3.11 (tt, J=12.0, 3.6, 1H), 2.87 (br. t, J approx. 12, 2H), 1.85 (m, 2H), 1.61 (m, 2H), 1.49 (s, 9H).

What is claimed is:

1. The present invention provides a process for the preparation of compounds of structural formula (VII):

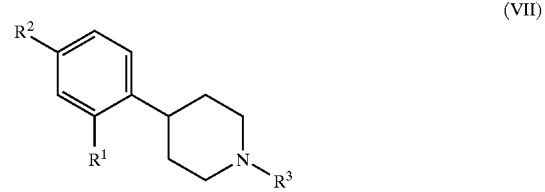

(VII)

wherein
R$^1$ is selected from the group consisting of
  (1) CN,
  (2) C(O)OH,
  (3) C(O)—C$_{1-6}$ alkyl,
  (4) C(O C$_{1-6}$ alkyl)$_2$—C$_{1-6}$ alkyl, and
  (5) C(R$^5$)$_2$N(R$^5$)C(O)—C$_{1-6}$ alkyl;
each R$^2$ is independently selected from the group consisting of
  (1) hydrogen,
  (2) C$_{1-6}$ alkyl,
  (3) —(CH$_2$)$_n$-phenyl,
  (4) —(CH$_2$)$_n$-naphthyl,
  (5) —(CH$_2$)$_n$-heteroaryl,
  (6) —(CH$_2$)$_n$-heterocyclyl,
  (7) —(CH$_2$)$_n$C$_{3-7}$ cycloalkyl,
  (8) fluoride,
  (9) chloride,
  (10) OR$^5$,
  (11) —(CH$_2$)$_n$N(R$^5$)$_2$,
  (12) —(CH$_2$)$_n$C≡N,
  (13) —(CH$_2$)$_n$CO$_2$R$^5$,
  (14) NO$_2$,

(15) N(R⁵)₂,
(16) —(CH₂)ₙNR⁵SO₂R⁵,
(17) —(CH₂)ₙSO₂N(R⁵)₂,
(18) —(CH₂)ₙS(O)ₚR⁵,
(19) —(CH₂)ₙNR⁵C(O)N(R⁵)₂,
(20) —(CH₂)ₙC(O)N(R⁵)₂,
(21) —(CH₂)ₙNR⁵C(O)R⁵,
(22) —(CH₂)ₙNR⁵CO₂R⁵,
(23) —(CH₂)ₙNR⁵C(O)-heteroaryl,
(24) —(CH₂)ₙC(O)NR⁵N(R⁵)₂,
(25) —(CH₂)ₙC(O)NR⁵NR⁵C(O)R⁵,
(26) O(CH₂)ₙC(O)N(R⁵)₂,
(27) CF₃,
(28) CH₂CF₃,
(29) OCF₃, and
(30) OCH₂CF₃, wherein phenyl, naphthyl, heteroaryl, cycloalkyl, and heterocyclyl are unsubstituted or substituted with one to three substituents independently selected from halogen, hydroxy, oxo, $C_{1-4}$ alkyl, trifluoromethyl, and $C_{1-4}$ alkoxy, and wherein any methylene (CH₂) carbon atom in R² is unsubstituted or substituted with one to two groups independently selected from halogen, hydroxy, and $C_{1-4}$ alkyl, or two substituents when on the same methylene (CH₂) group are taken together with the carbon atom to which they are attached to form a cyclopropyl group;

R³ is selected from the group consisting of
(1) C(O)O-phenyl,
(2) C(O)O—CH₂-phenyl,
(3) C(O)O-isopropyl,
(4) C(O)O-isobutyl, and
(5) C(O)O-ethyl;

each R⁵ is independently selected from the group consisting of
(1) hydrogen,
(2) $C_{1-6}$ alkyl,
(3) —(CH₂)ₙ-phenyl,
(4) —(CH₂)ₙ-heteroaryl,
(5) —(CH₂)ₙ-naphthyl,
(6) —(CH₂)ₙ-heterocyclyl,
(7) —(CH₂)ₙ$C_{3-7}$ cycloalkyl, and
(8) —(CH₂)ₙ$C_{3-7}$ bicycloalkyl, wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy, or two R⁵ groups together with the atom to which they are attached form a 4- to 8-membered mono- or bicyclic ring system optionally containing an additional heteroatom selected from O, S, and —N$C_{1-4}$ alkyl;

comprising the steps of:
(a) preparing a compound of structural formula (IV)

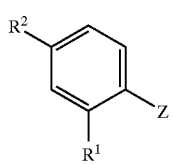

(IV)

wherein
R¹ and R² are as defined above, and Z is a halogen atom selected from the group consisting of bromide and iodide, by halogenating a compound of structural formula (III)

(III)

wherein
R¹ and R² are as defined above, and isolating the resulting product;
(b) forming an aryl magnesium halide of structural formula (V)

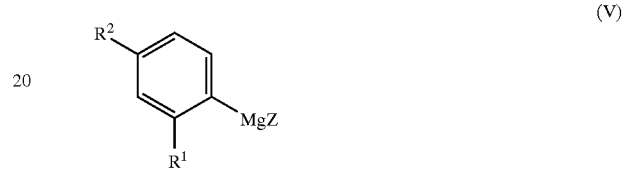

(V)

wherein R¹, R² and Z are as defined above,
by treating the compound of structural formula (IV) with a magnesium compound;
(c) preparing a compound of structural formula (VI)

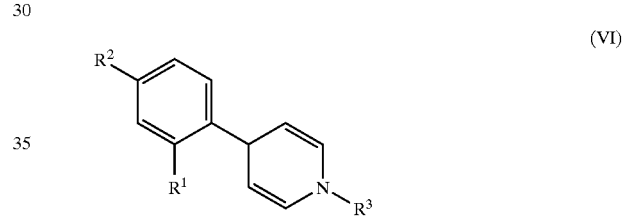

(VI)

wherein R¹, R² and R³ are as defined above,
by treating the aryl magnesium halide of structural formula (V)

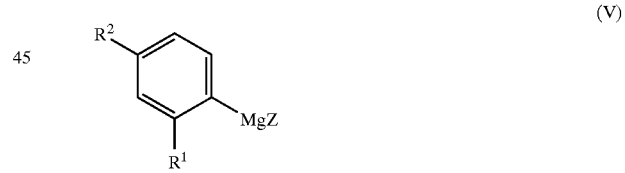

(V)

wherein R¹, R², and Z are as defined above, with a preformed pyridinium ion, and isolating the resulting product;
(d) reducing the dihydropyridine double bonds in the compound of structural formula (VI)

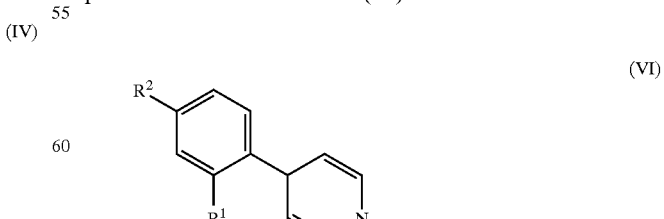

(VI)

wherein R¹, R² and R³ are as defined above; and
(e) isolating the resulting product.

2. The process of claim 1 wherein $R^1$ is CN; $R^2$ is chloride; $R^3$ is C(O)O—CH$_2$-phenyl; and Z is bromide.

3. The process of claim 2 wherein the compound of structural formula (III) is brominated by treatment with a brominating agent in the presence of an acid.

4. The process of claim 3 wherein the brominating agent is 1,3-dibromo-5,5-dimethylhydantoin.

5. The process of claim 3 wherein the acid is methane sulfonic acid.

6. The process of claim 1 step (b) wherein the magnesium compound is a compound of formula (IX)

wherein $R^a$ is selected from the group consisting of isopropyl, cyclohexyl and tert-butyl, and X is selected from the group consisting of chloride, bromide, and iodide.

7. The process of claim 6 wherein the magnesium compound of formula (X) is isopropyl magnesium chloride.

8. The process of claim 1 wherein the preformed pyridinium ion of step (c) is formed by treating pyridine, with a chloroformate of formula (X)

wherein $R^b$ is selected from the group consisting of ethyl, isopropyl, isobutyl, phenyl and benzyl, in the presence of a copper compound.

9. The process of claim 8 wherein the copper compound is copper iodide.

10. The process of claim 8 wherein the chloroformate of formula (X) is benzyl chloroformate.

11. The process of claim 1 wherein the dihydropyridine double bonds of compound (VI) of step (d) are reduced by hydrogenation in the presence of a catalyst.

12. The process of claim 11 wherein the catalyst is RhCl(PPh$_3$)$_3$.

13. The process of claim 1 further comprising the steps of (f) cleaving the $R^3$ protecting group in the compound of structural formula (VII)

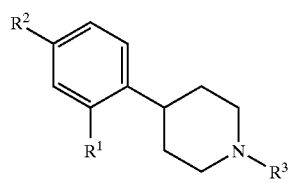

wherein $R^1$, $R^2$, and $R^3$ are as defined in claim 1, to afford a compound of structural formula (VIII)

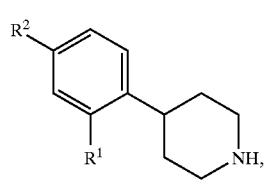

and isolating the resulting product;
(g) adding a $R^4$ protecting group to the free amine (VIII) to form the compound of structural formula (I),

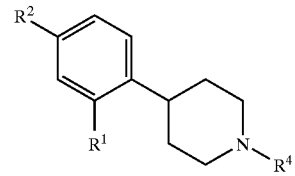

wherein $R^1$, $R^2$ are as defined above, and
$R^4$ is selected from the group consisting of
(1) C(O)O-tert-butyl,
(2) C(O)O—CH$_2$-phenyl, and
(3) C(O)O-phenyl; and
(h) isolating the resulting product.

14. The process of claim 13 wherein $R^4$ is C(O)O-tert-butyl.

15. A process for preparing a compound of structural formula (I)

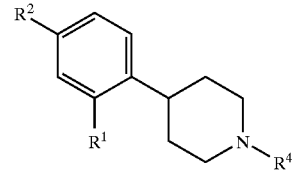

comprising the steps of:
(a) preparing a compound of structural formula (IV)

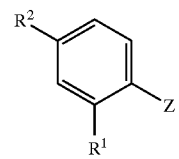

by halogenating a compound of structural formula (III)

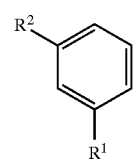

and isolating the resulting product;
(b) forming an aryl magnesium halide of structural formula (V)

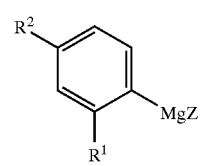

by treating the compound of structural formula (IV) with a magnesium compound;

(c) preparing a compound of structural formula (VI)

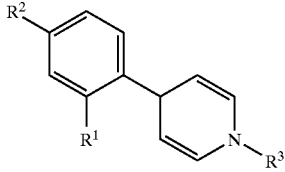

(VI)

by treating the aryl magnesium halide of structural formula (V)

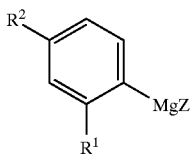

(V)

with a preformed pyridinium ion, and isolating the resulting product;

(d) reducing the dihydropyridine double bonds in the compound of structural formula (VI)

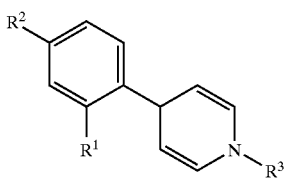

(VI)

and (e) isolating the resulting product;

wherein $R^1$ is selected from the group consisting of
(1) CN,
(2) C(O)OH,
(3) C(O)—$C_{1-6}$ alkyl,
(4) C(O$C_{1-6}$ alkyl)$_2$—$C_{1-6}$ alkyl, and
(5) C($R^5$)$_2$N($R^5$)C(O)—$C_{1-6}$ alkyl;

each $R^2$ is independently selected from the group consisting of
(1) hydrogen,
(2) $C_{1-6}$ alkyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$-heterocyclyl,
(7) —(CH$_2$)$_n$C$_{3-7}$ cycloalkyl,
(8) fluoride,
(9) chloride,
(10) O$R^5$,
(11) —(CH$_2$)$_n$N($R^5$)$_2$,
(12) —(CH$_2$)$_n$C≡N,
(13) —(CH$_2$)$_n$CO$_2$$R^5$,
(14) NO$_2$,
(15) N($R^5$)$_2$,
(16) —(CH$_2$)$_n$N$R^5$SO$_2$$R^5$,
(17) —(CH$_2$)$_n$SO$_2$N($R^5$)$_2$,
(18) —(CH$_2$)$_n$S(O)$_p$$R^5$,
(19) —(CH$_2$)$_n$N$R^5$C(O)N($R^5$)$_2$,
(20) —(CH$_2$)$_n$C(O)N($R^5$)$_2$,
(21) —(CH$_2$)$_n$N$R^5$C(O)$R^5$,
(22) —(CH$_2$)$_n$N$R^5$CO$_2$$R^5$,
(23) —(CH$_2$)$_n$N$R^5$C(O)-heteroaryl,
(24) —(CH$_2$)$_n$C(O)N$R^5$N($R^5$)$_2$,
(25) —(CH$_2$)$_n$C(O)N$R^5$N$R^5$C(O)$R^5$,
(26) O(CH$_2$)$_n$C(O)N($R^5$)$_2$,
(27) CF$_3$,
(28) CH$_2$CF$_3$,
(29) OCF$_3$, and
(30) OCH$_2$CF$_3$, wherein phenyl, naphthyl, heteroaryl, cycloalkyl, and heterocyclyl are unsubstituted or substituted with one to three substituents independently selected from halogen, hydroxy, oxo, $C_{1-4}$ alkyl, trifluoromethyl, and $C_{1-4}$ alkoxy, and wherein any methylene (CH$_2$) carbon atom in $R^2$ is unsubstituted or substituted with one to two groups independently selected from halogen, hydroxy, and $C_{1-4}$ alkyl, or two substituents when on the same methylene (CH$_2$) group are taken together with the carbon atom to which they are attached to form a cyclopropyl group;

$R^3$ is selected from the group consisting of
(1) C(O)O-phenyl,
(2) C(O)O—CH$_2$-phenyl,
(3) C(O)O-isopropyl,
(4) C(O)O-isobutyl, and
(5) C(O)O-ethyl;

$R^4$ is selected from the group consisting of
(1) C(O)O-tert-butyl,
(2) C(O)O—CH$_2$-phenyl, and
(3) C(O)O-phenyl; and each $R^5$ is independently selected from the group consisting of
(1) hydrogen,
(2) $C_{1-6}$ alkyl,
(3) —(CH$_2$)$_n$-phenyl,
(4) —(CH$_2$)$_n$-heteroaryl,
(5) —(CH$_2$)$_n$-naphthyl,
(6) —(CH$_2$)$_n$-heterocyclyl,
(7) —(CH$_2$)$_n$C$_{3-7}$ cycloalkyl, and
(8) —(CH$_2$)$_n$C$_{3-7}$ bicycloalkyl, wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy, or two $R^5$ groups together with the atom to which they are attached form a 4- to 8-membered mono- or bicyclic ring system optionally containing an additional heteroatom selected from O, S, and —N$C_{1-4}$ alkyl; and Z is a halogen atom selected from the group consisting of bromide and iodide.

16. The process of claim 15 wherein $R^1$ is CN; $R^2$ is chloride; $R^3$ is C(O))—CH$_2$-phenyl; $R^4$ is C(O)O-tert-butyl; and Z is bromide.

17. The process of claim 16 wherein the compound of structural formula (III) is brominated by treatment with a brominating agent in the presence of an acid.

18. The process of claim 17 wherein the brominating agent is 1,3-dibromo-5,5-dimethylhydantoin.

19. The process of claim 17 wherein the acid is methanesulfonic acid, trifluoroacetic acid, or sulfuric acid, or a combination thereof.

20. The process of claim 15 step (b) wherein the magnesium compound is a compound of formula (IX)

wherein $R^a$ is selected from the group consisting of isopropyl, cyclohexyl and tert-butyl, and X is selected from the group consisting of chloride, bromide, and iodide.

21. The process of claim 20 wherein the magnesium compound of formula (X) is isopropyl magnesium chloride.

22. The process of claim 15 wherein the preformed pyridinium ion of step (c) is formed by treating pyridine, with a chloroformate of formula (X)

wherein $R^b$ is selected from the group consisting of ethyl, isopropyl, isobutyl, phenyl and benzyl, in the presence of a copper compound.

23. The process of claim 22 wherein the copper compound is copper iodide.

24. The process of claim 22 wherein the chloroformate of formula (X) is benzyl chloroformate.

25. The process of claim 15 wherein the dihydropyridine double bonds of compound (VI) of step (d) are reduced by hydrogenation in the presence of a catalyst and an anhydride.

26. The process of claim 25 wherein the catalyst is Pd/C.

27. The process of claim 25 wherein the anhydride is tert-butyloxycarbonyl anhydride.

28. A process for preparing a compound of structural formula (I)

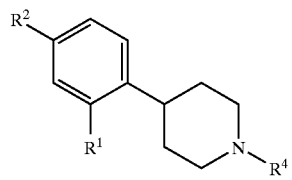

comprising the steps of:
(a) reducing the dihydropyridine double bonds in the compound of structural formula (VI)

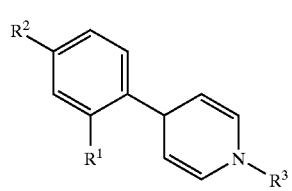

and
(b) isolating the resulting product;
wherein $R^1$ is selected from the group consisting of
  (1) CN,
  (2) C(O)OH,
  (3) C(O)—$C_{1-6}$ alkyl,
  (4) C(O$C_{1-6}$ alkyl)$_2$—$C_{1-6}$ alkyl, and
  (5) C($R^5$)$_2$N($R^5$)C(O)—$C_{1-6}$ alkyl;
each $R^2$ is independently selected from the group consisting of
  (1) hydrogen,
  (2) $C_{1-6}$ alkyl,
  (3) —(CH$_2$)$_n$-phenyl,
  (4) —(CH$_2$)$_n$-naphthyl,
  (5) —(CH$_2$)$_n$-heteroaryl,
  (6) —(CH$_2$)$_n$-heterocyclyl,
  (7) —(CH$_2$)$_n$$C_{3-7}$ cycloalkyl,
  (8) fluoride,
  (9) chloride,
  (10) O$R^5$,
  (11) —(CH$_2$)$_n$N($R^5$)$_2$,
  (12) —(CH$_2$)$_n$C≡N,
  (13) —(CH$_2$)$_n$CO$_2$$R^5$,
  (14) NO$_2$,
  (15) N($R^5$)$_2$,
  (16) —(CH$_2$)$_n$N$R^5$SO$_2$$R^5$,
  (17) —(CH$_2$)$_n$SO$_2$N($R^5$)$_2$,
  (18) —(CH$_2$)$_n$S(O)$_p$$R^5$,
  (19) —(CH$_2$)$_n$N$R^5$C(O)N($R^5$)$_2$,
  (20) —(CH$_2$)$_n$C(O)N($R^5$)$_2$,
  (21) —(CH$_2$)$_n$N$R^5$C(O)$R^5$,
  (22) —(CH$_2$)$_n$N$R^5$CO$_2$$R^5$,
  (23) —(CH$_2$)$_n$N$R^5$C(O)-heteroaryl,
  (24) —(CH$_2$)$_n$C(O)N$R^5$N($R^5$)$_2$,
  (25) —(CH$_2$)$_n$C(O)N$R^5$N$R^5$C(O)$R^5$,
  (26) O(CH$_2$)$_n$C(O)N($R^5$)$_2$,
  (27) CF$_3$,
  (28) CH$_2$CF$_3$,
  (29) OCF$_3$, and
  (30) OCH$_2$CF$_3$,
wherein phenyl, naphthyl, heteroaryl, cycloalkyl, and heterocyclyl are unsubstituted or substituted with one to three substituents independently selected from halogen, hydroxy, oxo, $C_{1-4}$ alkyl, trifluoromethyl, and $C_{1-4}$ alkoxy, and wherein any methylene (CH$_2$) carbon atom in $R^2$ is unsubstituted or substituted with one to two groups independently selected from halogen, hydroxy, and $C_{1-4}$ alkyl, or two substituents when on the same methylene (CH$_2$) group are taken together with the carbon atom to which they are attached to form a cyclopropyl group;
$R^3$ is selected from the group consisting of
  (1) C(O)O-phenyl,
  (2) C(O)O—CH$_2$-phenyl,
  (3) C(O)O-isopropyl,
  (4) C(O)O-isobutyl, and
  (5) C(O)O-ethyl;
$R^4$ is selected from the group consisting of
  (1) C(O)O-tert-butyl,
  (2) C(O)O—CH$_2$-phenyl, and
  (3) C(O)O-phenyl; and
each $R^5$ is independently selected from the group consisting of
  (1) hydrogen,
  (2) $C_{1-6}$ alkyl,
  (3) —(CH$_2$)$_n$-phenyl,
  (4) —(CH$_2$)$_n$-heteroaryl,
  (5) —(CH$_2$)$_n$-naphthyl,
  (6) —(CH$_2$)$_n$-heterocyclyl,
  (7) —(CH$_2$)$_n$$C_{3-7}$ cycloalkyl, and
  (8) —(CH$_2$)$_n$$C_{3-7}$ bicycloalkyl,
wherein alkyl, phenyl, heteroaryl, heterocyclyl, and cycloalkyl are unsubstituted or substituted with one to three groups independently selected from halogen, $C_{1-4}$ alkyl, hydroxy, and $C_{1-4}$ alkoxy, or two $R^5$ groups together with the atom to which they are attached form a 4- to 8-membered mono- or bicyclic ring system optionally containing an additional heteroatom selected from O, S, and —$NC_{1-4}$ alkyl.

29. The process of claim 28 wherein $R^1$ is CN; $R^2$ is chloride; $R^3$ is C(O)O—$CH_2$-phenyl; and $R^4$ is C(O)O-tert-butyl.

30. The process of claim 28 wherein the dihydropyridine double bonds of compound (VI) of step (d) are reduced by hydrogenation in the presence of a catalyst and an anhydride.

31. The process of claim 30 wherein the catalyst is Pd/C.

32. The process of claim 30 wherein the anhydride is tert-butyloxycarbonyl anhydride.

33. The compound 1-6

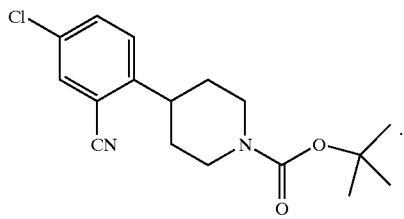

1-6

34. The compound 1-5

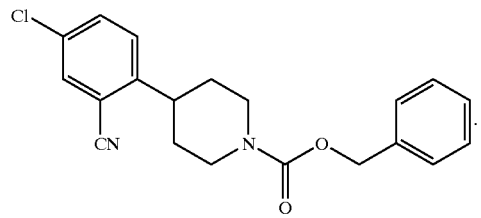

1-5

35. The compound 1-4

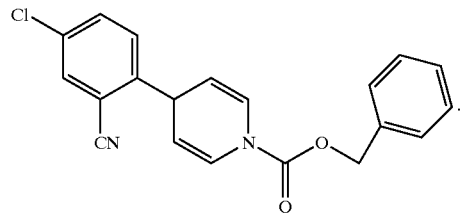

1-4

* * * * *